(12) United States Patent
Halliday

(10) Patent No.: US 12,245,945 B2
(45) Date of Patent: Mar. 11, 2025

(54) PROSTHESIS FOR ACETABULUM FRACTURES

(71) Applicant: EO-SOL GmbH, Innsbruck (AT)

(72) Inventor: David Edward Halliday, Duesseldorf (DE)

(73) Assignee: EO-SOL GmbH, Innsbruck (AT)

( * ) Notice: Subject to any disclaimer, the term of this patent is extended or adjusted under 35 U.S.C. 154(b) by 569 days.

(21) Appl. No.: 17/602,197

(22) PCT Filed: Apr. 6, 2020

(86) PCT No.: PCT/EP2020/059702
§ 371 (c)(1),
(2) Date: Oct. 7, 2021

(87) PCT Pub. No.: WO2020/207938
PCT Pub. Date: Oct. 15, 2020

(65) Prior Publication Data
US 2022/0211508 A1 Jul. 7, 2022

(30) Foreign Application Priority Data
Apr. 8, 2019 (LU) ........................ 101171

(51) Int. Cl.
*A61F 2/34* (2006.01)
*A61B 17/80* (2006.01)
*A61F 2/30* (2006.01)

(52) U.S. Cl.
CPC ............ *A61F 2/34* (2013.01); *A61B 17/8066* (2013.01); *A61F 2002/30449* (2013.01); *A61F 2002/30462* (2013.01); *A61F 2002/3069* (2013.01); *A61F 2002/3401* (2013.01); *A61F 2002/3448* (2013.01)

(58) Field of Classification Search
CPC ............ A61F 2/34; A61F 2002/30462; A61B 17/8066; A61B 17/82; A61B 17/842
See application file for complete search history.

(56) References Cited

U.S. PATENT DOCUMENTS

| 6,416,553 | B1 | 7/2002 | White et al. |
| 10,231,762 | B2 * | 3/2019 | Steinhauer ........... A61B 17/842 |
| 2003/0060890 | A1 | 3/2003 | Tarabishy |

FOREIGN PATENT DOCUMENTS

| EP | 0605368 A1 | 7/1994 |
| WO | 03075801 A1 | 9/2003 |

* cited by examiner

*Primary Examiner* — Brian A Dukert
(74) *Attorney, Agent, or Firm* — Kagan Binder, PLLC

(57) ABSTRACT

The present invention is related to a prosthesis, in particular a revision prosthesis, for repositioning and fixating acetabulum fractures. The prosthesis comprises a cup member (1), a hook member (2) and a hook retraction member (3). The cup member is formed and configured to be fixable into an acetabular cup. The hook member is formed and configured to be fixable onto an edge of the acetabular cup. The cup member and the hook member are formed and configured to be retractable into one another. The hook retraction member comprises at least one cable arranged and configured for retracting the hook member into the cup member.

Figure 1A:
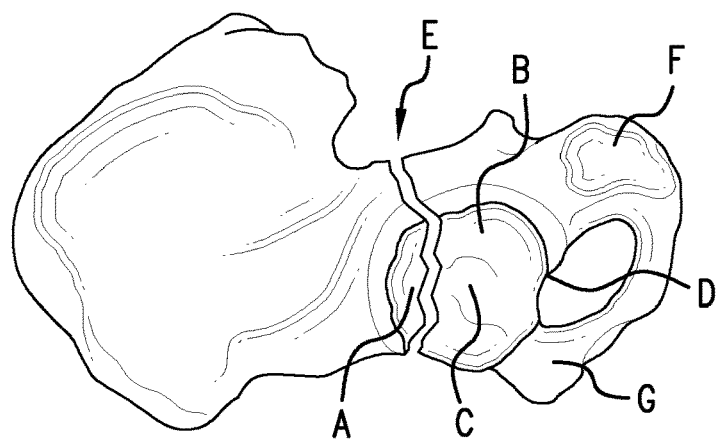

16 Claims, 8 Drawing Sheets

PROSTHESIS FOR ACETABULUM FRACTURES

PRIORITY CLAIM

This application claims priority to International Application No. PCT/EP2020/059702, filed Apr. 6, 2020, which claims priority to Luxembourg Application No. 101171, filed Apr. 8, 2019 wherein the contents of said applications are incorporated herein by reference in their entireties.

The present invention is related to a prosthesis, in particular a revision prosthesis, for repositioning and fixating acetabulum fractures.

The acetabulum or rather the acetabular cup of a human being or an animal may be fractured. Such acetabulum fracture, besides causing pain, disables the subject by rendering usage of the respective leg impossible. During implantation of a hip prosthesis the acetabulum may fracture while an acetabular cup of the hip prosthesis is fixated to the acetabulum or while the acetabulum is prepared for said cup. During revision of a hip prosthesis acetabulum fractures are frequent due to reduced bone stability in the proximity of the hip prosthesis. Also in case of a hip luxation the acetabulum may be fractured. Further, elderly people are especially prone to fractionising the acetabulum due to reduced bone density.

Said acetabulum fractures occur in three subjects per 1000 subjects per year (3/1000/a). The incidence of transversal acetabulum fractures is 8.3% [percent] and the incidence of transversal fractures of the posterior wall of the acetabulum is 17.4%.

In order to mend the fractured bone parts of the acetabulum must be arranged in the original orientation and brought into contact or at least proximity to each other. As the hip is one of the most stressed joints in a human or animal body mere reposition of the bone parts and immobilisation is not sufficient for acceptable healing of acetabulum fractures.

It is known to reposition the bone parts of a fractured acetabular cup with a prosthesis having a cup member. At the cup member a hook is attached, which hook is fixable onto edge of the acetabular cup. The bone parts of the acetabular cup are fixated at the cup member of the prosthesis with bone screws.

However, the bone parts of the acetabular cup may be positioned next to each other by means of the known prosthesis without sufficient approximation such that mending of the bone parts is impeded or even prevented.

It is an objective of the present invention to overcome or at least alleviate the above mentioned drawbacks. For this purpose the present invention provides a prosthesis, in particular a revision prosthesis, for repositioning and fixating acetabulum fractures according to independent claim 1. Further refinements of the present invention are subject of the dependent claims.

According to a first aspect of the present invention a prosthesis, in particular a revision prosthesis, for repositioning and fixating acetabulum fractures comprises a cup member, a hook member and a hook retraction member. Alternatively or additionally to the hook member and the hook retraction member the cup member comprises two or more cup shells and the prosthesis further comprises a cup retraction member. The cup member is formed and configured to be fixable into an acetabular cup. The hook member is formed and configured to be fixable onto an edge of the acetabular cup. The cup member and the hook member are formed and configured to be retractable into one another. The hook retraction member comprises at least one cable arranged and configured for retracting the hook member into the cup member. Each of the two cup shells is formed and configured to be fixable into one of two or more proximal halves of the acetabular cup having a transverse fracture. The cup retraction member comprises at least one cable arranged and configured for retracting the two ore more cup shells towards each other.

According to a second aspect of the present invention a method of repositioning and fixating acetabulum fractures with a prosthesis, in particular a revision prosthesis, comprises the steps:

Fixating a cup member into an acetabular cup;
Fixating a hook member onto an edge of the acetabular cup, wherein the cup member and the hook member are formed and configured to be retractable into one another;
Retracting the hook member into the cup member by means of a retraction member comprising at least one cable.

In case of an acetabulum fracture the acetabular cup is fractured at least into a first bone part and a second bone part.

The cup member is fixated into the first bone part of the acetabular cup and the hook member is fixated onto the edge of the second pone part of the acetabular cup. The cup member and alternatively or additionally the hook member may be fixated onto the respective bone part by means of at least one bone screw. The two bone parts of the acetabular cup are repositioned onto each other by retracting the hook member into the cup member (retracted position). Repositioning in this context means aligning the bone parts in their original position to each other and closing any gap between the two bone parts of the acetabular cup such that the two parts can mend together. Additionally, a predefined pressure of the two bone parts onto each other can be applied by retracting the hook member into the cup member with a respective tension.

The hook member may be formed such that it exactly fits into the cup member in the retracted position. Consequently, there cannot be any displacement of the cup member against the hook member in the retracted position and the first and second bone part cannot be displaced any more.

In order to retract the hook member into the cup member, the at least one cable of the hook retraction member is pulled (e.g. by a surgeon or otherwise qualified person) such that the hook member with the second bone part is retracted into the cup member with the first bone member. Thereby, the first bone part and the second bone part are brought back into contact with each other in the original orientation or position. Original orientation or position in this context means that the two bone parts are aligned in each of the three directions in space (x, y, z) and also in each of the three angles in space ($\varphi$, $\rho$, $\tau$) to each other such that the acetabular cup is realigned according to the original acetabular cup before the acetabulum fracture.

The at least one cable of the hook retraction member may be guided along the surface of the cup member or inside the cup member. The at least one cable may be guided along the cup member by means of guiding elements like guiding brackets, guiding eyes or guiding holes. The cables may be guided in a first guiding direction parallel to a first retraction direction of the hook member into the cup member. In case the hook retraction member comprises more than one cable the respective guiding direction of each of the cables may deviate up to 90° [degree] from the first retraction direction of the hook member.

The at least one cable may be fixated in the pulled back position and thereby the hook member remains retracted into the cup member. Consequently, the second bone part is positioned in contact to or at least proximity of the first bone part, whereby the two bone parts are aligned to each other in their original position. For example the at least one cable may be fixated in the pulled back position where the hook member is retracted into the cup member (retracted position) by means of a husk that is clamped onto the at least one cable such that the husk is in contact with one of the guiding elements, preferably the last guiding element in the guiding direction.

The cup member may be a predefined standard cup member in different predefined sizes (like S, M, L and XL). The hook member may be a predefined standard hook member in predefined different sizes. Each standard hook member may fit into each standard cup member in the retracted position. For each acetabular cup the hook member and alternatively or additionally the cup member may be made to measure for optimal fit. In Particular, the hook member and alternatively or additionally the cup member may be made by 3D-printing or rapid prototyping. Preferably, the cup member is a predefined standard cup member and the hook member is made to measure.

Each of the cup shells can be fixated onto one of the proximal halves of the acetabular cup. In this case one fracture of the acetabulum fracture separates the two or more proximal halves, here together the first bone part that has the transverse fracture, of the acetabular cup from each other. A further lateral fracture may separate the two or more proximal halves (together the first bone part) of the acetabular cup from the remaining bone part, here the second bone part, or multiple bone parts. The two or more cup shells are retracted towards each other in a second or further retraction direction(s) by means of the cup retraction member.

For example the cup member may comprise three cup shells each fixated onto one bone part. Each of the cup shells can be retracted towards the other two cup shells via the cup retraction member such that the bone parts can be moved towards and pressed onto each other (i.e. be repositioned). It is also possible that the cup member may comprise four or even more cup shells each fixated onto one bone part.

The at least one cable of the cup retraction member may be guided along the two or more cup shells or inside the two or more cup shells in a guiding direction parallel to the second or further retraction direction(s) by means of guiding elements like guiding brackets, guiding eyes or guiding holes.

If the cup retraction member comprises more than one cable, the respective guiding direction of each of the cables may deviate up to 90° [degree] from the second or further retraction direction(s) of the hook member.

With the prosthesis according to the present invention the bone parts of an acetabular cup, in case of an acetabulum fracture, can be repositioned and fixated onto each other in the original position such that the bone parts of the acetabular cup can optimally mend together. With the prosthesis having a retractable hook member and two or more retractable cup shells the bone parts (two or more proximal halves and second bone part) of a threefold or manifold acetabulum fracture including at least a transversal and a lateral fracture of the acetabular cup can be repositioned in the optimal orientation to each other such that the acetabular cup can mend.

According to a refinement of the present invention the prosthesis further comprises at least one fixation plate connected to the cup member and formed and configured to be fixable at an ilium.

The at least one fixation plate may be an integral part of the prosthesis and manufactured in one piece with the cup member.

Alternatively, the fixation plate may be an additional part that is fixated to the cup member by force locking and/or form fitting and/or adhesion and/or cohesion.

The at least one fixation plate may be attached to the ilium by means of bone screws.

The at least one fixation plate may be made to measure for optimal fit. Further, the at least one fixation plate may be made by 3D-printing or rapid prototyping.

The at least one fixation plate fixated at the ilium further increases stability of the connection of the cup member with the acetabular cup.

According to a refinement of the present invention the cup member is formed and configured to be fixable into a proximal part of the acetabular cup having a lateral fracture.

The cup member can be fixated into the proximal part of the acetabular cup. In this case one fracture of the acetabulum fracture separates the proximal part, here the first bone part, of the acetabular cup from the remaining bone part, here the second bone part, or multiple remaining bone parts.

According to a refinement of the present invention the hook member is formed and configured to be fixable onto a distal part of the edge of the acetabular cup having the lateral fracture.

The hook member can be fixated onto the distal part of the edge of the acetabular cup. In this case one fracture of the acetabulum fracture separates the distal part of the edge, here the second bone part, of the acetabular cup from the remaining bone part, here the first bone part, or multiple bone parts.

According to a refinement of the present invention the prosthesis further comprises a pubis plate and a pubis retraction member and alternatively or additionally an ischium plate and an ischium retraction member. The pubis plate is formed and configured to be fixable onto a pubis. The pubis retraction member comprises at least one cable arranged and configured for retracting the pubis plate towards the cup member. The ischium plate is formed and configured to be fixable onto an ischium. The ischium retraction member comprises at least one cable arranged and configured for retracting the ischium plate towards the cup member.

Additionally to the hook member fixated onto the edge of the second bone part the ischium plate fixated to the ischium and alternatively or additionally the pubis plate fixated to the pubis can be retracted towards the cup member by means of the ischium retraction member and the pubis retraction member, respectively.

The at least one cable of the ischium retraction member and the at least one cable of the pubis retraction member, respectively, may be guided along the cup member or inside the cup member by means of guiding elements. The guiding elements may be guiding brackets, guiding eyes or guiding holes. The ischium plate and the pubis plate, respectively, may be retracted along a third retraction direction and along a fourth retraction direction, respectively, towards the cup member. The guiding elements may guide the respective at least one cable along the corresponding retraction direction.

The ischium plate and the pubis plate, respectively, may be fixated to the ischium and pubis, respectively, by means of bone screws.

The ischium plate and alternatively or additionally the pubis plate may be made to measure and in particular made by 3D-printing or rapid prototyping.

The prosthesis with the additional ischium plate and additionally or alternatively the pubis plate offers a more stable fixation of the acetabular fracture. Additionally, the bone parts can be repositioned more precisely, because the additional retraction members offer addition degrees of freedom during repositioning of the bone parts.

According to a further refinement of the present invention the hook retraction member is arranged and configured to be fixated in a retracted position where the hook member is retracted into the cup member.

When the hook member is retracted into the cup member in the retracted position, the bone parts (first and second bone part) of the acetabular fracture are repositioned in the optimal orientation to each other. In this retracted position the hook member has to be secured against the cup member. The cable of the hook retraction member having been pulled back into the pulled back position such that the hook member is in the retracted position can be fixated in the pulled back position by various means like a husk that is pushed along the cable until it is in contact with the last guiding element (guiding bracket, guiding eye or guiding hole) in the retraction direction, where the husk is crimped and thus secured against the guiding element.

The prosthesis with the hook retraction member that can be fixated in the retracted position can safely stabilise the repositioned acetabulum fracture.

According to a further refinement of the present invention the cup retraction member is arranged and configured to be fixated in a retracted position where the two cup shells are retracted at each other and alternatively or additionally wherein the pubis retraction member is arranged and configured to be fixated in a retracted position where the pubis plate is retracted at the cup member and alternatively or additionally wherein the ischium retraction member is arranged and configured to be fixated in a retracted position where the ischium plate is retracted at the cup member.

When the two cup shells are retracted at each other, the two proximal halves of the acetabular cup (together the first bone part) of the threefold acetabular fracture are repositioned in the optimal orientation to each other. In this retracted position the two cup shells have to be secured against each other. The at least one cable of the cup retraction member having been pulled back such that the two cup shells are in the retracted position can be fixated in this position by various means like a husk that is pushed along the cable until it is in contact with the last guiding element (guiding bracket, guiding eye or guiding hole) in the retraction direction, where the husk is crimped and thus secured against the guiding element. Likewise the at least one cable of the ischium retraction member and the at least one cable of the pubis retraction member, respectively, can be fixated in the respective position where the ischium plate and the pubis plate, respectively, are retracted towards the cup member.

The prosthesis with the cup retraction member, ischium retraction member and pubis retraction member, respectively, which can be fixated in the respective retracted position, can safely stabilise the repositioned threefold acetabulum fracture.

According to a refinement of the present invention the prosthesis further comprises an inlay cup for an artificial hip that is formed and configured to be fitted into the cup member.

The inlay cup can be fitted intraoperatively into the cup member after the acetabulum fracture has been repositioned and fixated by the prosthesis. The inlay cup may be directly fitted into the cup member by pushing or driving (by impact) the inlay cup into the cup member until it snaps in place. The inlay cup and the cup member are manufactured with a precise fitting relative to each other.

The inlay cup may be made of polymeric material or ceramic material.

The prosthesis with fitting inlay cup for the artificial hip is in particular helpful in case of revision of a defect artificial hip where during the revision a acetabulum fracture occurs. The acetabulum fracture can be repositioned and stabilised while the artificial hip can still be replaced.

According to a further refinement of the present invention the inlay cup is fixated to the cup member by a layer of bone cement, preferably polymethyl methacrylate.

The inlay cup is placed in the cup member, after the acetabular fracture has been repositioned, in a bed of bone cement (polymethyl methacrylate). Then the inlay cup can be aligned as needed as long as the bone cement has not cured. When the inlay cup is aligned as desired the bone cement can cure and after curing, the artificial hip (artificial femoral head) can be fitted into the inlay cup.

The fixation of the inlay cup by means of bone cement is a particular easy and fast method for positioning the inlay cup in the cup member of the prosthesis.

According to a further refinement of the present invention the inlay cup is arranged and configured to be fixedly attached to a preferably metallic inlay cup member being arranged and configured to be positioned within the cup member and fixated thereto by means of at least one screw.

After the acetabular fracture has been repositioned, the inlay cup member is positioned in the cup member and fixated thereto with the at least one screw. Then the inlay cup is fixedly attached to the inlay cup member for example by pushing or driving the inlay cup into the inlay cup member. The inlay cup may precisely fit into the inlay cup member.

The two part design (inlay cup and corresponding inlay cup member) enables a particular precise orientation of the inlay cup in the prosthesis.

According to a further refinement of the present invention the cup member as well as the hook retraction member and alternatively or additionally the cup retraction member and alternatively or additionally the pubis retraction member and alternatively or additionally the ischium retraction member are configured such that the respective retraction member is fixated at the cup member in the respective retracted position by means of the layer of bone cement or the inlay cup member.

After the acetabulum fracture has been repositioned the at least one cable of the respective retraction member has to be secured in the respective retracted or pulled back position. Thereto, the respective cable(s) are fixated on the cup member either by means of the cured layer of bone cement or by the inlay cup being pressed onto the cup member and the respective cable(s) in-between due to the precise fitting between the cup member and the inlay cup.

With the fixation of the respective retraction member(s) by means of the layer of bone cement or the inlay cup no additional fixation elements are necessary.

According to a further refinement of the present invention the cup member and the inlay cup as well as the hook retraction member and/or the cup retraction member and/or the pubis retraction member and or the ischium retraction member are configured such that the respective retraction member is fixated in the respective retracted position by clamping the respective at least one cable between the cup member and the inlay cup member or the layer of bone cement.

With the two part design (inlay cup and inlay cup member) the respective cable(s) of the retraction member(s) are either fixated at the cup member by means of the cured layer of bone cement, which is applied before the inlay cup member is positioned and fixated in the cup member. Preferably, the respective cable(s) of the retraction member(s) are fixated at the cup member by the inlay cup member pressed onto the cup member by means of the at least one screw such that the cable(s) are clamped in between the cup member and the inlay cup member.

With the fixation of the respective retraction member(s) by means of the layer of bone cement or the inlay cup member no additional fixation elements are necessary.

According to a refinement of the present invention the hook retraction member comprises two cables, wherein the cables are aligned in parallel to each other along a first retraction direction along which the hook member is retracted into the cup member and/or wherein the cup retraction member comprises two cables, wherein the cables are aligned in parallel to each other along a second retraction direction along which the two cup shells are retracted towards each other.

The two cables of the hook retraction member may be guided by corresponding guide elements (guiding brackets, guiding eyes, guiding holes) along or inside the cup member. The two cables of the hook retraction member are guided in the first retraction direction such that the hook member can be retracted into the cup member by pulling on the two cables of the hook retraction member.

The two cables of the cup retraction member may be guided by corresponding guide elements (guiding brackets, guiding eyes, guiding holes) along or inside the two cup shells forming the cup member. The two cables of the cup retraction member are guided in the second retraction direction such that the two cup shells can be retracted towards each other by pulling on the two cables of the cup retraction member.

The respective retraction members having two cables aligned in the corresponding retraction direction enable an especially precise repositioning of the bone parts of the acetabulum fracture.

The pubis plate and additionally or alternatively the ischium plate may be retracted towards the cup member by means of one single cable. Preferably, the pubis plate and the ischium plate are retractable towards the cup member by means of two or more cables.

Any retractable member (hook member, pubis plate, ischium plate, cup shells) of the prosthesis may be retracted by means of one or more cable. The cable may be fixated at another member of the prosthesis towards which the retractable member is retractable. If the retractable member is retractable by means of two or more cables, the two or more cables may be separate cables fixed and guided separately or the two or more cables may be one cable that is fixed at separate points and guided in separate guiding directions.

According to a third aspect of the present invention a retraction prosthesis comprises a first plate member, a second plate member and a retraction member. The first plate member is formed and configured to be fixable at a first part of a bone fracture. The second plate member is formed and configured to be fixable at a second part of the bone fracture. The retraction member comprises at least one cable arranged and configured for retracting the second plate member towards the first plate member. The first plate member and the retraction member are configured such that the retraction member can be fixated at the first plate member in a retracted position where the second plate member is retracted at the first plate member by means of bone cement, preferably polymethyl methacrylate.

According to a fourth aspect of the present invention a method for fixating a retraction member of a retraction prosthesis comprises the steps:

Fixating a first plate member of the retraction prosthesis to a first part of a bone fracture.

Fixating a second plate member of the retraction prosthesis to a second part of the bone fracture.

Retracting the second plate member towards the first plate member by means of at least one cable of the retraction member.

Fixating the retraction member at the first plate member in a retracted position where the second plate member is retracted at the first plate member by means of bone cement, preferably polymethyl methacrylate.

The first plate member may be fixated to the first part of the bone fracture by means of bone screws and the second plate member may be fixated to the second part of the bone fracture by means of bone screws. The at least one cable of the retraction member may be guided along or inside the first and second plate member by means of guiding elements (guiding brackets, guiding eyes, guiding holes). By pulling on the at least one cable the second plate member can be retracted towards the first plate member in a retracted position. Consequently, the first and second part of the bone fracture can be realigned in said retracted position.

The retraction member is fixated at the first plate member in the retracted position by the bone cement. The bone cement secures the at least one cable at the first plate member when it has completely cured.

The fixation of the retraction member at the first plate member with bone cement no additional fixation elements are necessary.

Figure 2A:
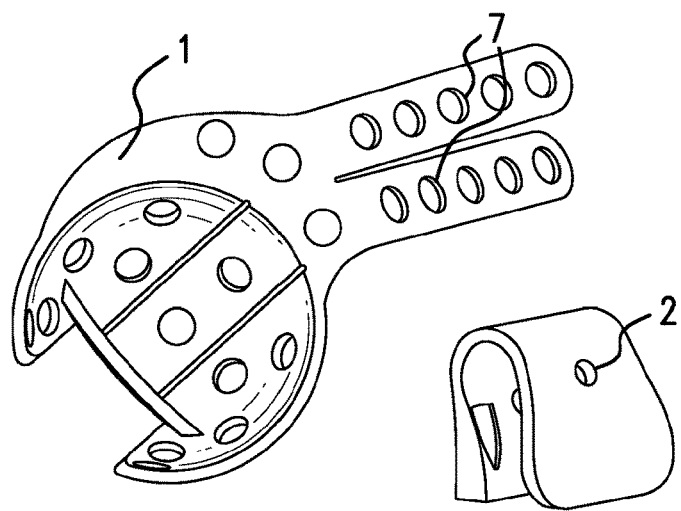
Figure 2B:
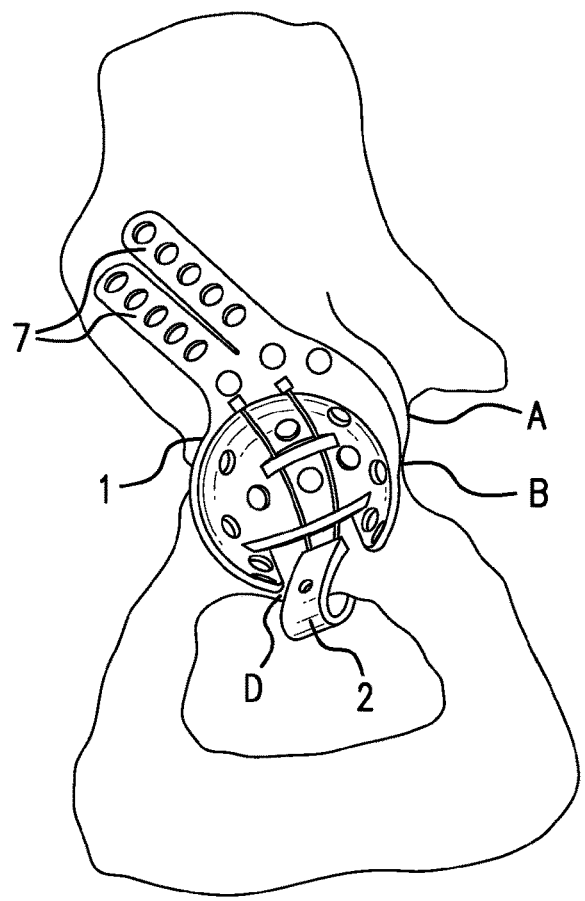
Figure 3:
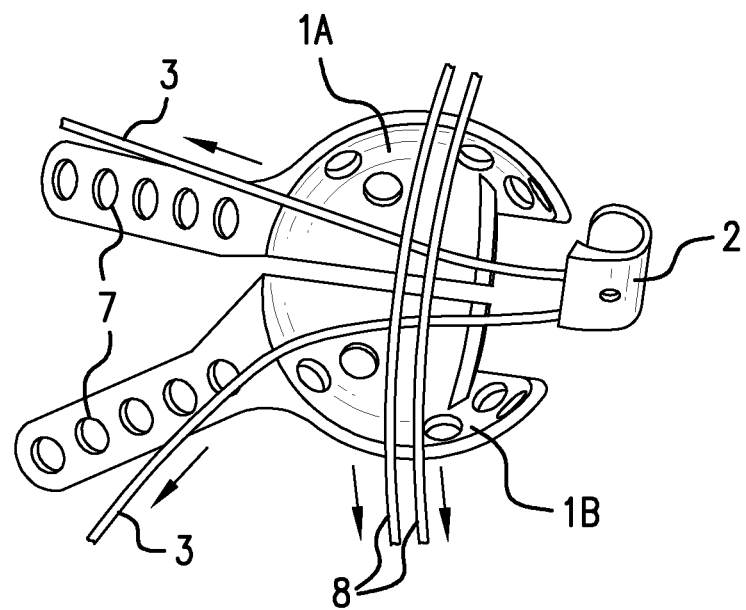
Figure 4:
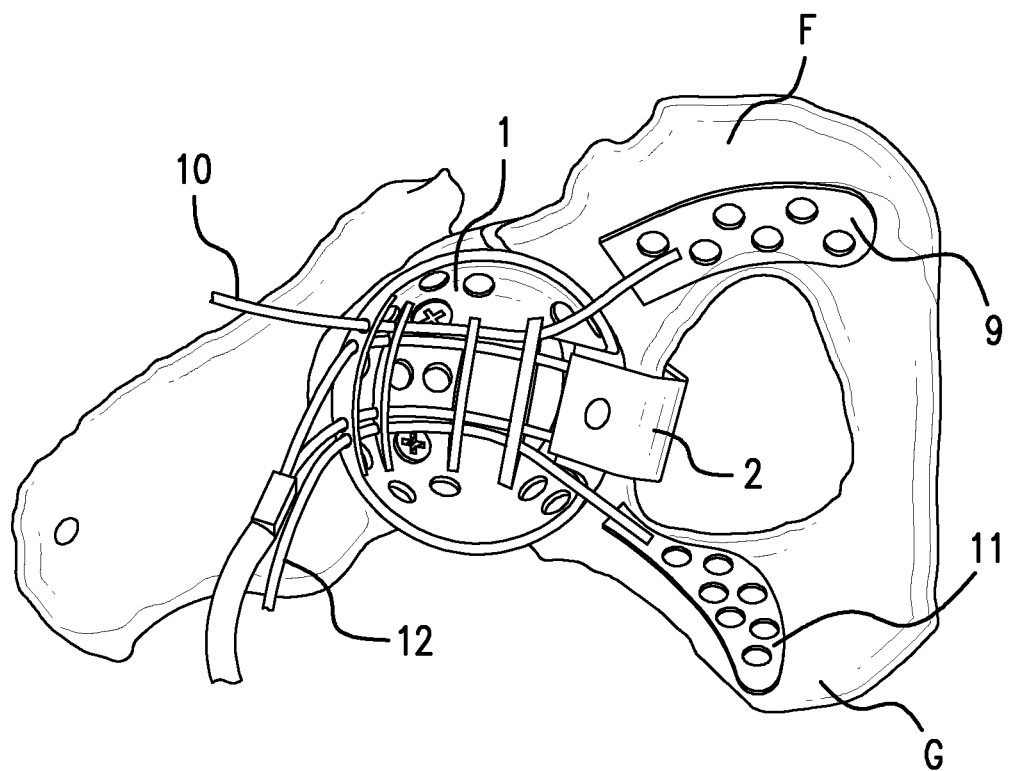
Figure 5:
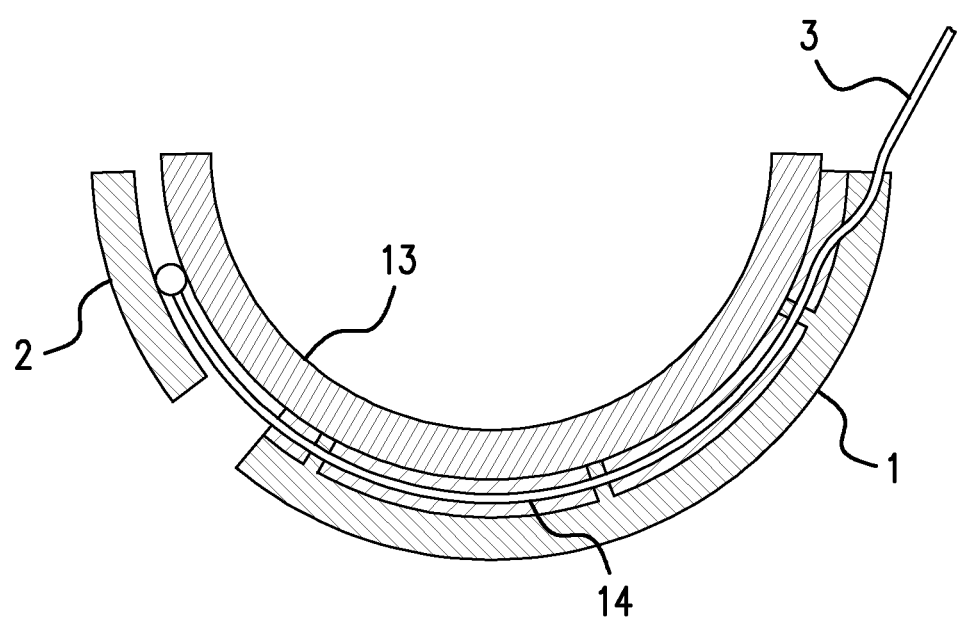
Figure 6A:
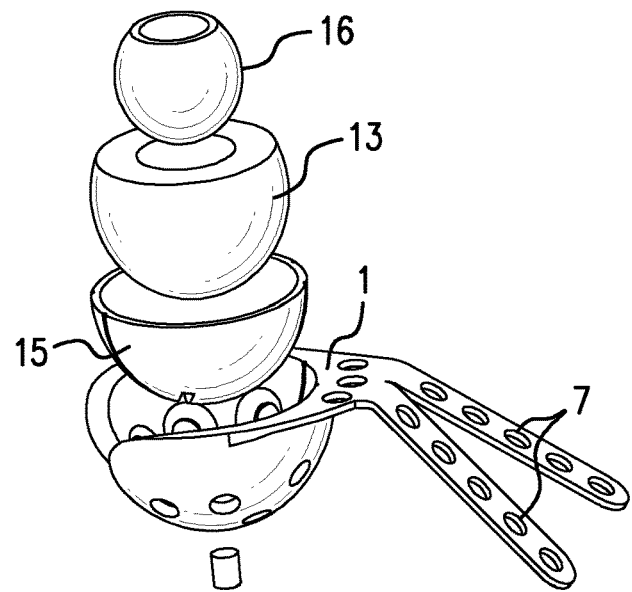
Figure 6B:
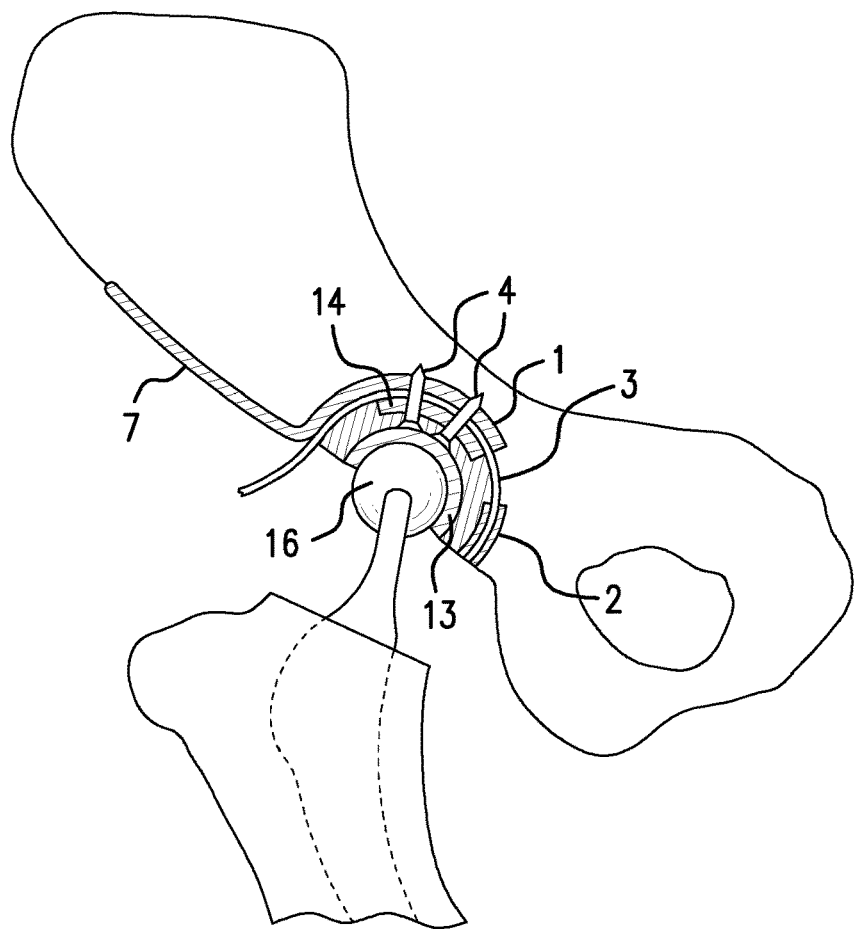
Figure 7:
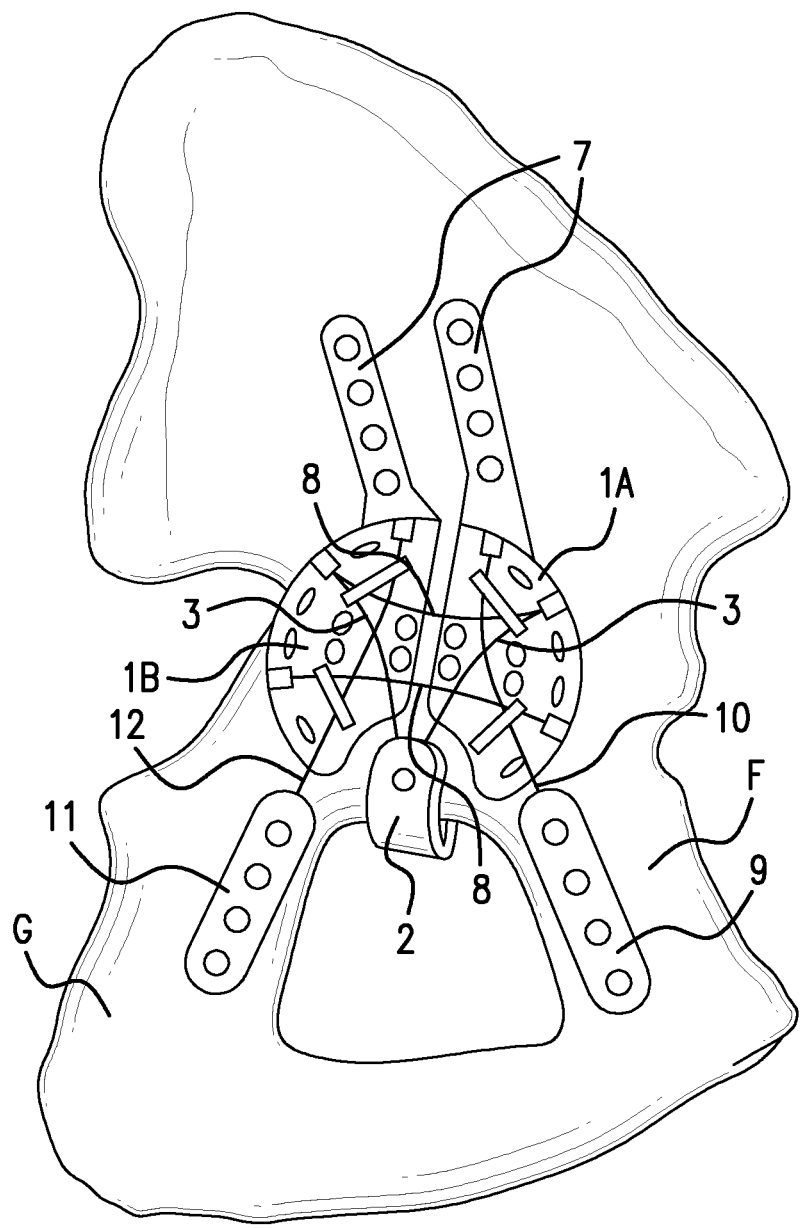
Figure 8:
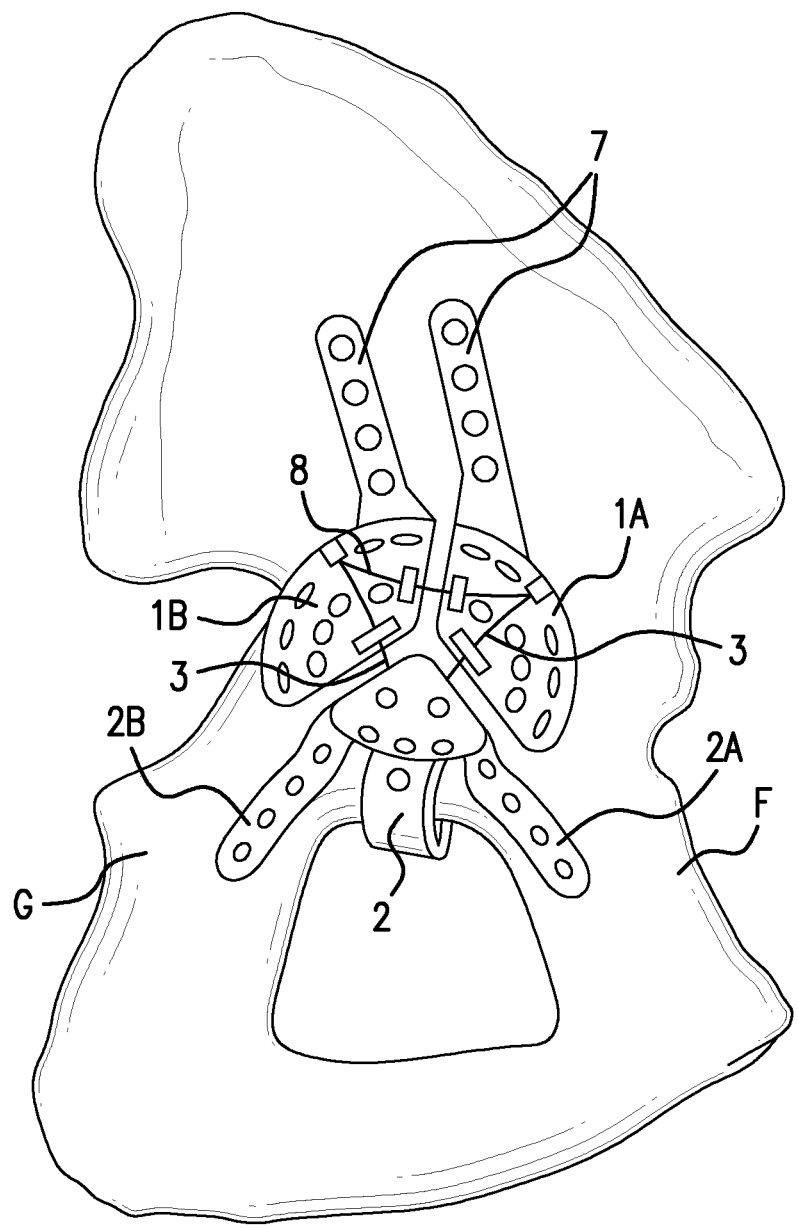

Preferred embodiments of the invention will be explained in the following, having regard to the drawings. It is shown in:

FIG. 1A-1D an acetabular fracture and a prosthesis for repositioning and fixating acetabulum fractures according to the present invention;

FIG. 2A-2B a further embodiment of the prosthesis for repositioning and fixating acetabulum fractures with additional fixation plates;

FIG. 3 a further embodiment of the prosthesis for repositioning and fixating acetabulum fractures with two cup shells;

FIG. 4 a further embodiment of the prosthesis for repositioning and fixating acetabulum fractures with a pubis plate and an ischium plate;

FIG. 5 a sectional view of the prosthesis with a layer of bone cement between a cup member and a inlay cup;

FIG. 6A-6B a further embodiment of the prosthesis for repositioning and fixating acetabulum fractures with an inlay cup and an inlay cup member;

FIG. 7 a further embodiment of the prosthesis for repositioning and fixating acetabulum fractures with two cup shells, a pubis plate and an ischium plate; and FIG. 8 a further embodiment of the prosthesis for repositioning and fixating acetabulum fractures with a hook having a pubis fixation plate and an ischium fixation plate.

In the following, preferred embodiments of the invention will be described with reference to the drawings. The same or similar elements or elements having the same effect may be indicated by the same reference number in multiple drawings.

Repeating the description of such elements may be omitted in order to prevent redundant descriptions.

In FIG. 1A an acetabulum fracture with a first bone part A and a second bone part B is schematically depicted. An acetabular cup C of the acetabulum with a distal part of an edge of the acetabular cup D has a lateral fracture E. The acetabulum further has a pubis F and an ischium G.

Figure 1B:
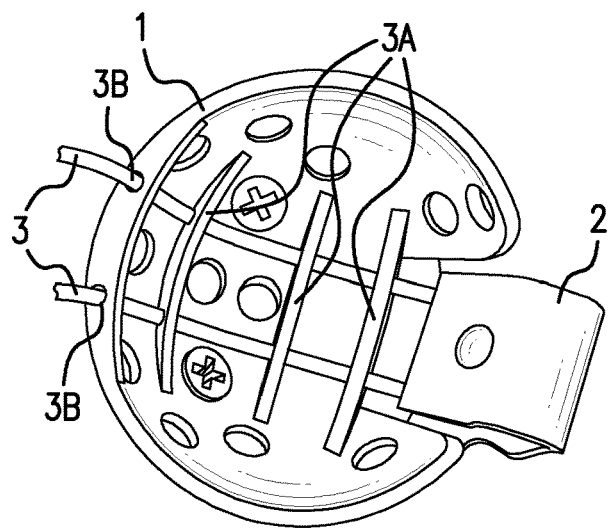

In FIG. 1B a prosthesis for repositioning and fixating acetabulum fractures is schematically depicted. The prosthesis comprises a cup member 1 and a hook member 2. The hook member 2 is retractable into the cup member 1 by means of a hook retraction member 3. The hook retraction member 3 comprises two cables but may comprise only one or more than two cables. The cables are guided by guiding eyes 3A and guiding holes 3B.

When the cables of the retraction member are pulled the hook member 2 is retracted into the cup member 1 (retracted position). The hook member 2 loosely or tightly fits into the cup member 1.

Figure 1C:
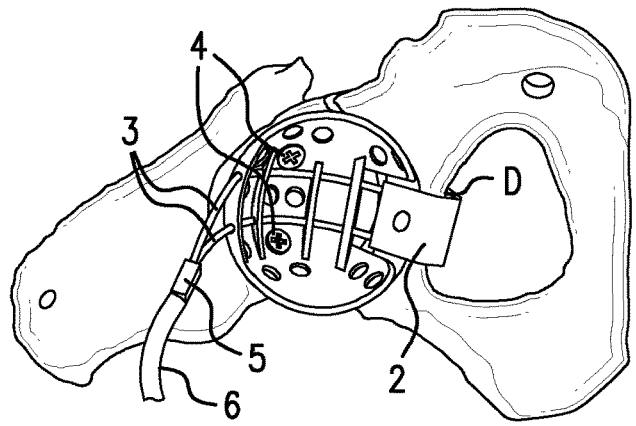

In FIG. 1C the acetabulum fracture repositioned and fixated by the prosthesis is schematically depicted. The cup member 1 is fixated with two bone screws to a proximal part of the acetabular cup, which is the first bone part (A). The hook member is placed around the distal end of the edge of the acetabular cup D, which is the second bone part (B) and fixated with one bone screw. The two cables of the hook retraction member are held together by a sleeve or husk 4. The acetabulum fracture is closed by pulling the cables of the hook retraction member 3 using a tensioner 6. The cables connect the hook member to the cup member and hence provide stability. The tension on the two cables of the hook retraction member is maintained while a crimp tool is placed around the husk 4. Then the husk 4 is crimped onto the two cables of the hook retraction member 3 in order to secure the cables and keep the hook member in the retracted position.

Figure 1D:
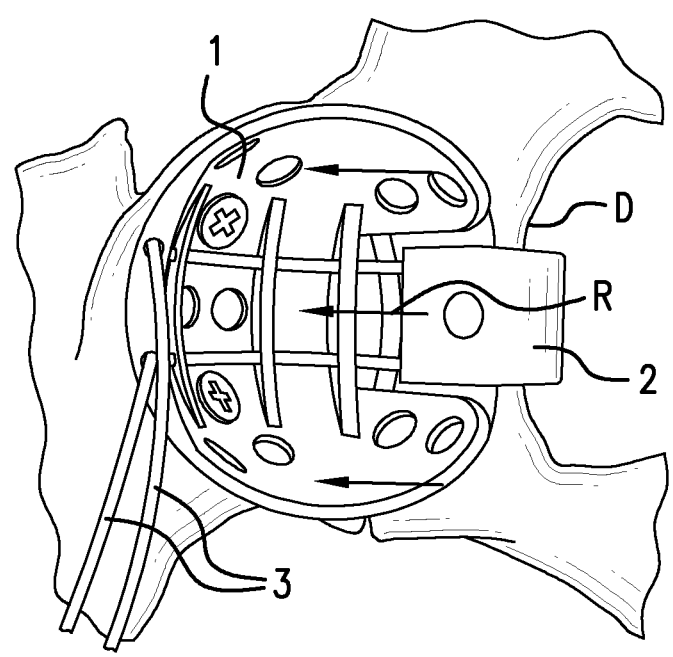

In FIG. 1D a retraction direction R is schematically depicted. The hook member 2 is retracted into the cup member 1 in the retraction direction R by pulling at the two cables of the hook retraction member 3. Here the two cables of the hook retraction member 3 are guided along the cup member 1 in parallel to the retraction direction R.

In FIG. 2A-2B a further embodiment of the prosthesis for repositioning and fixating is schematically depicted. Only the differences to the preceding embodiments are described in the following.

The prosthesis as depicted in FIG. 2A further comprises two fixation plates 7. The fixation plates 7 are fixedly attached to the cup member 1.

In FIG. 2B the acetabulum fracture repositioned and fixated by the prosthesis of FIG. 2A is schematically depicted. The cup member 1 and the hook member 2 are fixated like in FIG. 1B-1D. Here for further stability the fixation plates 7 are fixated each with at least one bone screw at an ilium of the acetabulum.

In FIG. 3 a further embodiment of the prosthesis for repositioning and fixating is schematically depicted. Only the differences to the preceding embodiments are described in the following. The cup member (1) is divided into two cup shells 1A, 1B. The prosthesis further comprises a cup retraction member 8 having two cables. The two cables of the cup retraction member 8 are guided along the cup member 1 in parallel to a second retraction direction.

The two cup shells 1A and 1B may each be fixated (e.g. with at least one bone screw) on one of the two bone parts of the proximal part of the acetabular cup (C) in case of a transversal fracture of the acetabular cup (C) at an threefold acetabulum fracture. By pulling on the cables of the cup retraction member 8 the two cup shells can be moved towards each other and the two bone parts of the proximal part of the acetabular cup (C) may hence be repositioned and fixated.

In FIG. 4 a further embodiment of the prosthesis for repositioning and fixating is schematically depicted. Only the differences to the preceding embodiments are described in the following. The prosthesis further comprises an pubis plate 9 and a corresponding pubis retraction member 10 as well as a ischium plate 11 and a corresponding ischium retraction member 12. The pubis retraction member 10 and the ischium retraction member 12 each comprise one cable. The cable of the pubis retraction member 10 is guided along the cup member 1 in parallel to a third retraction direction. The cable of the ischium retraction member 12 is guided along the cup member 1 in parallel to a fourth retraction direction.

The pubis plate 9 and the ischium plate provide additional stability for the repositioned acetabulum fracture.

In FIG. 5 a sectional view of the preceding embodiments of the prosthesis for repositioning and fixating acetabulum fractures is schematically depicted. After the hook member 2 and optionally the pubis plate (9) and the ischium plate (11) have been retracted into or towards the cup member 1 and optionally after the two cup shells (1a, 1B) have been retracted towards each other, the cables of the respective retraction member 3 (8, 10, 12) are fixated in the retracted position by means of a layer of bone cement 14 between the cup member 1 and a cup inlay 13 (or alternatively a cup inlay member 15 carrying the cup inlay 13).

The cup inlay 13 may receive an artificial femoral head (16) of an artificial hip. The inlay cup 13 is placed in the cup member 1 after the acetabulum fracture has been repositioned. Before the inlay cup 13 is placed in the cup member 1 a layer of bone cement 14 is applied to the cup member 1. Before the bone cement cures, the inlay cup has to be positioned as desired in the cup member 1. The layer of bone cement 14 fixates the cables of the respective retraction members 3 (8, 10, 12) and also fixates the inlay cup 13 in the cup member 1.

Additionally, the bone cement may be loaded with a compression force during curing leading to a higher resistance against tensions occurring afterwards during gait cycle.

In FIG. 6A-6B a further embodiment of the prosthesis for repositioning and fixating is schematically depicted. Only the differences to the preceding embodiments are described in the following.

The prosthesis as depicted in FIG. 6A comprises a inlay cup member 15 that can be fixated into the cup member 1 and that can receive the inlay cup 13.

In FIG. 6B a sectional view of the acetabulum fracture repositioned and fixated with the prosthesis of FIG. 6A is schematically depicted. The inlay cup member 14 is fixated at the cup member 1 with two bone screws 4. The cables of the hook retraction member 3 (and optionally of the cup retraction member 8, the pubis retraction member 10 and the ischium retraction member 12) are fixated by being clamped between the cup member 1 and the inlay cup member 15. Alternatively, the cables may be fixated by a layer of (pre-stressed) bone cement. The inlay cup 13 is snapped into the inlay cup member 15 and the artificial femoral head 16 is received by the inlay cup 13.

In FIG. 7 a further embodiment of the prosthesis for repositioning and fixating is schematically depicted. Only the differences to the preceding embodiments are described in the following. The prosthesis comprises two cup shells 1A, 1B as the cup member 1 with a corresponding cup retraction member 8 having two cables, a hook member 2 with a corresponding hook retraction member 3 having two cables, two fixation plates 7 each fixedly attached to one of the cup shells, a pubis plate 9 with a corresponding pubis retraction member 10 having one cable and a ischium plate 11 with a corresponding ischium retraction member 12 having one cable. The two cup shells 1A, 1B are each fixated at one part of the proximal acetabular cup having a transversal fracture. For additional stability of each of the cup shells 1A, 1B the corresponding fixation plate 7 is fixated at the ilium. The hook member 2 is fixated at the distal end of the edge of the acetabular cup or the second part (B) of the lateral fracture. The pubis plate 9 is fixated at the pubis and the ischium plate 11 is fixated at the ischium. The two halves of the proximal part of the acetabular cup are repositioned and the transversal fracture is closed by retracting the two cup shells 1A, 1B towards each other with the cup retraction member 8. The first bone part (A) and the second bone part (B) are repositioned and the lateral is fracture closed by retracting the hook member 2 into the cup member 1 with the hook retraction member 3 and additionally by retracting the pubis plate 9 and the ischium plate 11 towards the cup member 1 with the pubis retraction member 10 and the ischium retraction member 12.

In FIG. 8 a further embodiment of the prosthesis for repositioning and fixating is schematically depicted. Only the differences to the preceding embodiments are described in the following. The prosthesis comprises two cup shells 1A, 1B as the cup member 1 with a corresponding cup retraction member 8 having one cable, a hook member 2 with a corresponding hook retraction member 3 having two cables, two fixation plates 7 each fixedly attached to one of the cup shells, a pubis fixation plate 2A fixedly attached to the hook member 2 and a ischium fixation plate 2B fixedly attached to the hook member 2. The two cup shells 1A, 1B are each fixated at one part of the proximal acetabular cup having a transversal fracture. For additional stability of each of the cup shells 1A, 1B the corresponding fixation plate 7 is fixated at the ilium. The hook member 2 is fixated at the distal end of the edge of the acetabular cup or the second part (B) of the lateral fracture. The pubis fixation plate 2A is fixated at the pubis and the ischium fixation plate 2B is fixated at the ischium. The two halves of the proximal part of the acetabular cup are repositioned and the transversal fracture is closed by retracting the two cup shells 1A, 1B towards each other with the cup retraction member 8. The first bone part (A) and the second bone part (B) are repositioned and the lateral fracture is closed by retracting the hook member 2 into the cup member 1 with the hook retraction member 3. The pubis fixation plate 2A and the ischium fixation plate 2B provide additional stability to the hook member 2.

Although the invention has been illustrated and described in detail by the embodiments explained above, it is not limited to these embodiments. Other variations may be derived by the skilled person without leaving the scope of the attached claims.

Generally, "a" or "an" may be understood as singular or plural, in particular with the meaning "at least one", "one or more", etc., unless this is explicitly excluded, for example by the term "exactly one", etc.

In addition, numerical values may include the exact value as well as a usual tolerance interval, unless this is explicitly excluded.

Features shown in the embodiments, in particular in different embodiments, may be combined or substituted without leaving the scope of the invention.

The invention claimed is:

1. A prosthesis for repositioning and fixating acetabulum fractures, comprising:
a cup member formed and configured to be fixable into a portion of a fractured acetabular socket;
a hook member formed and configured to be fixable onto an edge of the other portion of the fractured acetabular socket, wherein the cup member and the hook member are formed and configured to be retractable into one another; and
a hook retraction member comprising at least one cable arranged and configured for retracting the hook member into the cup member by which the portions of the fractured acetabular socket are retracted towards one another.

2. The prosthesis according to claim 1, further comprising at least one fixation plate connected to the cup member and formed and configured to be fixable at an ilium.

3. The prosthesis according to claim 1, wherein the cup member is formed and configured to be fixable into a proximal part of the acetabular cup having a lateral fracture.

4. The prosthesis according to claim 1, wherein the hook member is formed and configured to be fixable onto a distal part of the edge of the acetabular cup having the lateral fracture.

5. The prosthesis according to claim 1, (a) further comprising a pubis plate formed and configured to be fixable onto a pubis and a pubis retraction member comprising at least one cable arranged and configured for retracting the pubis plate towards the cup member, (b) further comprising a ischium plate formed and configured to be fixable onto a ischium and a ischium retraction member comprising at least one cable arranged and configured for retracting the ischium plate towards the cup member, or both (a) and (b).

6. The prosthesis according to claim 1, wherein the hook retraction member is arranged and configured to be fixated in a retracted position where the hook member is retracted into the cup member.

7. The prosthesis according to claim 1, wherein the cup member comprises two or more cup shells and wherein each of the two or more cup shells is formed and configured to be fixable into one of two or more proximal halves of the acetabular cup having a transverse fracture, and the prosthesis further comprising a cup retraction member comprising at least one cable arranged and configured for retracting the two or more cup shells towards each other.

8. The prosthesis according to claim 7, (a) wherein the cup retraction member is arranged and configured to be fixated in a retracted position where the two cup shells are retracted at each other, (b) wherein the pubis retraction member is arranged and configured to be fixated in a retracted position where the pubis plate is retracted at the cup member, (c) wherein the ischium retraction member is arranged and configured to be fixated in a retracted position where the ischium plate is retracted at the cup member, or any combination of (a)-(c).

9. The prosthesis according to claim 1, further comprising an inlay cup for an artificial hip that is formed and configured to be fitted into the cup member.

10. The prosthesis according to claim 9, wherein the inlay cup is fixated to the cup member by a layer of bone cement, optionally the bone cement comprising polymethyl methacrylate.

11. The prosthesis according to claim 9, wherein the inlay cup is arranged and configured to be fixedly attached to a preferably metallic inlay cup member being arranged and configured to be positioned within the cup member and fixated thereto by means of at least one screw.

12. The prosthesis according to claim 10, wherein: (a) the hook retraction member is arranged and configured to be fixated in a retracted position where the hook member is retracted into the cup member, (b) the cup member as well as the hook retraction member and/or the cup retraction member are configured such that the respective retraction member is fixated at the cup member in the respective retracted position by means of the layer of bone cement or the inlay cup member (13), or both (a) and (b).

13. The prosthesis according to claim 12, wherein: (a) the cup member and the inlay cup as well as the hook retraction member, (b) the cup retraction member, (c) the pubis retraction member, (d) the ischium retraction member, or any combination of (a)-(d), are configured such that the respective retraction member is fixated in the respective retracted position by clamping the respective at least one cable between the cup member and the inlay cup member or the layer of bone cement.

14. The prosthesis according to claim 1, wherein: (a) the hook retraction member comprises two cables, wherein the cables are aligned in parallel to each other along a first retraction direction along which the hook member is retracted into the cup member; (b) wherein the cup retraction member comprises two cables, wherein the cables are aligned in parallel to each other along a second retraction direction along which the two cup shells are retracted towards each other, or both (a) and (b).

15. A retraction prosthesis, comprising:
a first plate member formed and configured to be fixable at a first part of a bone fracture;
a second plate member formed and configured to be fixable at a second part of the bone fracture; and
a retraction member comprising at least one cable arranged and configured for retracting the second plate member towards the first plate member,
wherein the first plate member and the retraction member are configured such that the retraction member can be fixated at the first plate member in a retracted position with bone cement where the second plate member is retracted at the first plate member, optionally wherein the bone cement comprises polymethyl methacrylate.

16. The prosthesis according to claim 12, wherein (a) the cup retraction member is arranged and configured to be fixated in a retracted position where the two cup shells are retracted at each other, (b) wherein the pubis retraction member is arranged and configured to be fixated in a retracted position where the pubis plate is retracted at the cup member, (c) wherein the ischium retraction member is arranged and configured to be fixated in a retracted position where the ischium plate is retracted at the cup member, wherein (i) the cup member as well as the hook retraction member, (ii) the cup retraction member, (iii) the ischium retraction member, or any combination of (i)-(iii) are configured such that the respective retraction member is fixated at the cup member in the respective retracted position by means of the layer of bone cement or the inlay cup member.

* * * * *